United States Patent [19]
Yasuda et al.

[11] Patent Number: 5,378,635
[45] Date of Patent: Jan. 3, 1995

[54] METHOD OF MEASURING A CATECHOLAMINE AND ITS METABOLITE

[75] Inventors: Kenji Yasuda, Tokyo; Masami Aoki, Katsuta; Takefumi Yokokura, Tomobe, all of Japan

[73] Assignee: Hitachi, Ltd., Tokyo, Japan

[21] Appl. No.: 132,549

[22] Filed: Oct. 6, 1993

[30] Foreign Application Priority Data

Oct. 20, 1992 [JP] Japan ................... 4-280375

[51] Int. Cl.6 .............. G01N 21/65; G01N 33/74
[52] U.S. Cl. .................. 436/111; 436/172; 436/175; 436/800; 436/813
[58] Field of Search .............. 436/106, 107, 111, 172, 436/175, 800, 813

[56] References Cited

U.S. PATENT DOCUMENTS 4,680,272  7/1987  Smith ................... 436/86

OTHER PUBLICATIONS

F. A. J. Van der Hoorn et al., Journal of Chromatography, 487, pp. 17-28 (1989).

Primary Examiner—James C. Housel
Assistant Examiner—David Redding
Attorney, Agent, or Firm—Kenyon & Kenyon

[57] ABSTRACT

A method of measuring at least one of a catecholamine and its metabolite including a biological sample pretreatment process, a fluorescence inducing process of converting into a fluorescence inductor the at least one of a catecholamine and its metabolite in the biological sample subjected to pretreatment by means of a fluorescence inducing reagent, and a measuring process of separating and measuring said fluorescence inductor by liquid chromatography, said method being characterized by addition of a specified volume of maleimide before said process of making the biological sample fluorescent.

7 Claims, 3 Drawing Sheets

METHOD OF MEASURING A CATECHOLAMINE AND ITS METABOLITE

BACKGROUND OF THE INVENTION (1) Field of the Invention

The present invention relates to a method of, an apparatus for and a reagent for measuring a catecholamine and its metabolite in a biological sample.

(2) Description of the Prior Art

A measuring error is known to occur due to the presence of a substance which interferences with the fluorescence inducing reaction in the measure of separating catecholamine after the fluorophore containing catecholamine by liquid chromatography and converting the fluorophore of catecholamines in body fluids such as blood, urine and spinal fluid. As a solution of this problem, a method of adding N-ethylmaleimide represented by the following equation is reported (F. A. J. Van der Hoorn et al., Journal of Chromatography, 487, pp 17–28 (1989)).

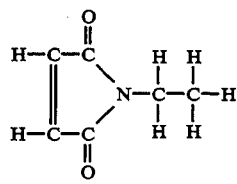

FIG. 2 illustrates the fluorescent chromatogram of urine analyzed by chromatography. It shows that the peak of catecholamines such as norepinephrine, epinephrine and dopamine contained in the urine is very low. The inhibition of inducing reaction is observed in other body fluids such as blood and spinal fluid.

Said reaction inhibition can be prevented by addition of the substance which would react with the interfering substance in advance and prevent interruption of the fluorescence inducing reaction. However, the conventional additive, N-ethylmaleimide itself causes a fluorescent peak. Therefore, it is very difficult to distinguish between the N-ethylmaleimide fluorescent peak and that of the catecholamine in the biological sample having the retention time adjacent to said peak. This has been a factor causing identification errors, leading to a failure in obtaining correct concentration of the catecholamines. A big peak occurs immediately in the retention time of norepinephrine, one of the catecholamines, especially in the case of the conventional N-ethylmaleimide. It has been found out that the measurements of catecholamines and their metabolites are adversely affected by the peak of 3,4-dihydroxyphenylethyleneglycol (DOPEG), one of the catecholamine metabolites, located contiguous to this position.

Especially, the concentration of catecholamines in the blood plasma is very low, causing a severe impact of the peak given by said interfering substance, and disabling measurement in some cases. Furthermore, the same peak occurs even if the retention time is reduced to some extent, resulting in difficulties, according to a recent finding.

SUMMARY OF THE INVENTION

An object of the present invention is to provide a measuring means which does not affect the peak of catecholamines and their metabolites.

Another objector the present invention is to provide an apparatus for measuring said catecholamines and their metabolites.

A further object of the present invention is to provide a reagent measuring said catecholamines and their metabolites.

In an effort to solve this problem, the inventors studied interference inhibition substances which did not produce fluorescent peaks, and succeeded in finding out that maleimide without alkyl chain has excellent characteristics, arriving at the present invention. The following gives a summary of the present invention:

(1) A method of measuring at least one of a catecholamine and its metabolite including a biological sample pretreatment process, a fluorescence inducing process of converting into a fluorescence inductor the catecholamine and its metabolite in the biological sample subjected to pretreatment by means of a fluorescence inducing reagent, and a measuring process of separating and measuring said fluorescence inductor by liquid chromatography, said method being characterized by adding a specified volume of maleimide before said process of making the biological sample fluorescent.

(2) A method according to (1), which is characterized by including a pretreatment process where said biological sample is put into a sample vessel supplied with a specified volume of maleimide in advance, and is mixed with a maleimide solution.

(3) A method according to (1), which is characterized in that maleimide in solid form and its solute are separate, and are then mixed together before said process of making the biological sample fluorescent.

Said maleimide can be represented by the following equation; it can be added in the process of transferring the biological sample to the fluorescence inducing process.

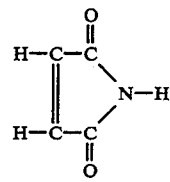

The fluorescence inducing reagent may include 1,2-diphenylethylenediamine and/or ethylenediamine.

Said maleimide fails to prevent said interfering substance, unless maleimide concentration is set within the appropriate range for the biological sample. However, excessive addition also prevents conversion of the catecholamine and its metabolites into the fluorescence inductor, so 10 to 60 m mol/l or preferably 20 to 50 m mol/l should be recommended in terms of concentration of the solution mixed with the biological sample.

A measuring apparatus used is the one comprising a sample dispensing means such as a syringe to dispense a specified volume of the biological sample, a pretreatment means linked to the sample dispensing means and pre-treating the biological sample, a fluorescent means to make the pre-treated biological sample fluorescent by the fluorescence inducing reagent, a separation column to separate the fluorescence inductor by chromatography, a flow cell to detect the fluorescence intensity of the fluorescence inductor separated by the separation column and a means to add a specified volume of maleimide to either the sample dispensing means or the pretreatment means for the biological sample. The measuring apparatus is preferably provided with a central processing unit to calculate and store the fluorescence intensity of the fluorescence inductor detected by the flow cell, and an output means such as a cathode ray tube (CRT) or printer to output the fluorescence intensity stored in the central processing unit.

The measuring apparatus can be made into a fully automated one by said CRT measuring instrument when a means is provided for controlling liquid pumps and valves by means of the central processing unit.

The maleimide used for the present invention is unstable in the form of solution, and should be prepared immediately before use, or should preferably be added directly to the biological sample. Therefore, maleimide in solid form such as in granular, pulverized or powder form is put in the vessel such as a polypropylene bag in advance, and is used as a biological sample vessel. Another preferable method is to prepare a reagent kit comprising a reagent bottle containing the pulverized maleimide and a reagent bottle containing the borate buffer solution; and the two solutions are mixed and dissolved immediately before use. The sample vessel and reagent bottle need not have any special form and material; they can be selected of any of the products available on the market if they are clean.

Maleimide is likely to react with SH compounds and amino acids in the body fluid, and is considered to prevent the SH compound and the amino acid from reacting with the fluorescence inducing reagent of catecholamines, thereby inhibiting the interference of fluorescence inducing reaction. Therefore, addition of maleimide after fluorescence inducing reaction cannot prevent the above action caused by the interfering component of the biological sample.

DESCRIPTION OF THE PREFERRED EMBODIMENTS

Embodiments or, the present invention will be described with reference to Figures.

Embodiment 1

50 ml of the urine of the healthy person is sampled, and 1.0 ml of the sampled urine is dilute to 1/100 in the pretreatment process. Then 1.0 ml of it was taken, and 100 µl of maleimide solution (pH 7.3) of 200 mM was added to it. Then 400 µl of acetonitrile dilute sulfuric acid solution of 1% 1,2-diphenylethylenediamine and 400 µl of the mixed aqueous solution of potassium ferricyanide and ammonium molybdate were added to it, and were heated to 50° C., obtaining fluorescence inductor in five minutes.

Figure 1:
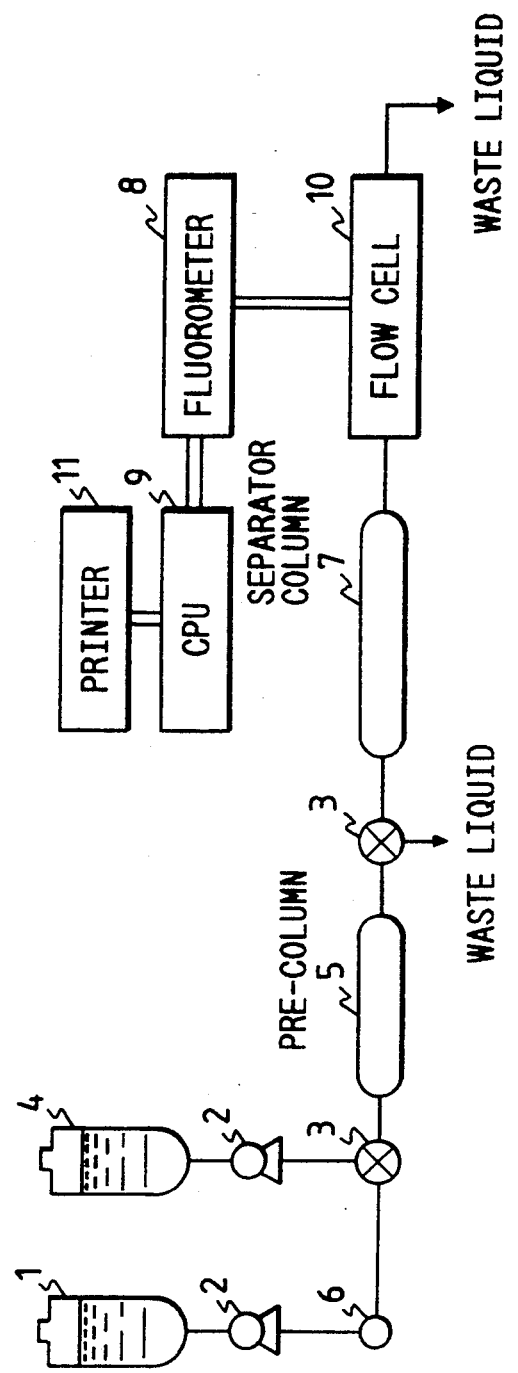
FIG. 1 is a block diagram of a catecholamine and its metabolite measuring apparatus showing an example according to the present invention.

100 µl of sample solution of said fluorescence inductor is supplied from inlet port 6 by the microsyringe into the high-speed liquid chromatography device which is connected with pre-column 5 filled with methacrylate resin and separator column 7 and which has a configuration shown in FIG. 1, so that the fluorescence inductor of the catecholamines was adsorbed to pre-column 5.

The switch valve 3 was switched so that eluant 4 comprising the solvent mixture of methanol and acetonitrile was led to pre-column 5 and separator column 7, and fluorescence inductor adsorbed to pre-column 5 was eluted and separated by separator column 7.

Components after separation of the fluorescence inductor were led to flow cell 10, and their fluorescence intensity was measured by fluorometer 9 at excitation wavelength of 350 nm and fluorescent wavelength of 500 nm. Fluorescence intensity detected by fluorometer 8 was recorded into the memory of CPU 9, and the recorded data was printed out by printer 11.

Figure 3:
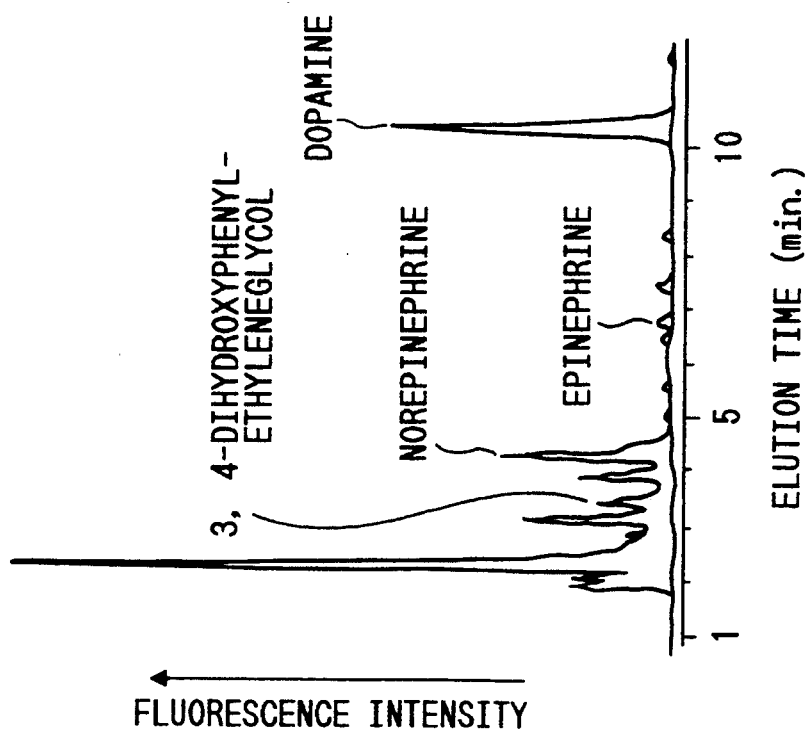
FIG. 3 illustrates a chromatogram of catecholamines contorted in urine with maleimide added.
Figure 2:
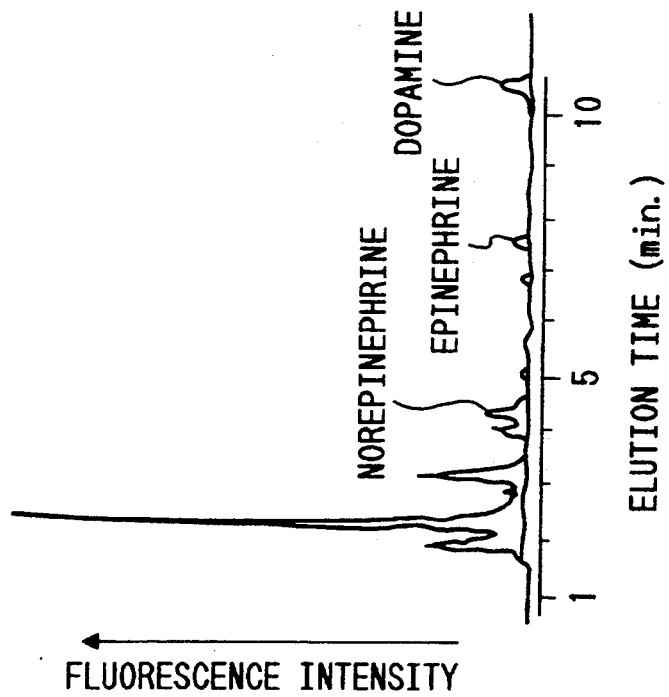
FIG. 2 illustrates a chromatogram of catecholamines contained in urine without interfering substances being removed.

FIG. 2 illustrates the chromatogram when the maleimide solution is not added, while FIG. 3 illustrates the chromatogram when the maleimide solution is added.

The peak of norepinephrine and dopamine when the maleimide solution is not added, is extremely small. However, both peaks are known to exhibit correct concentration without being interfered, if maleimide solution is added.

Figure 4:
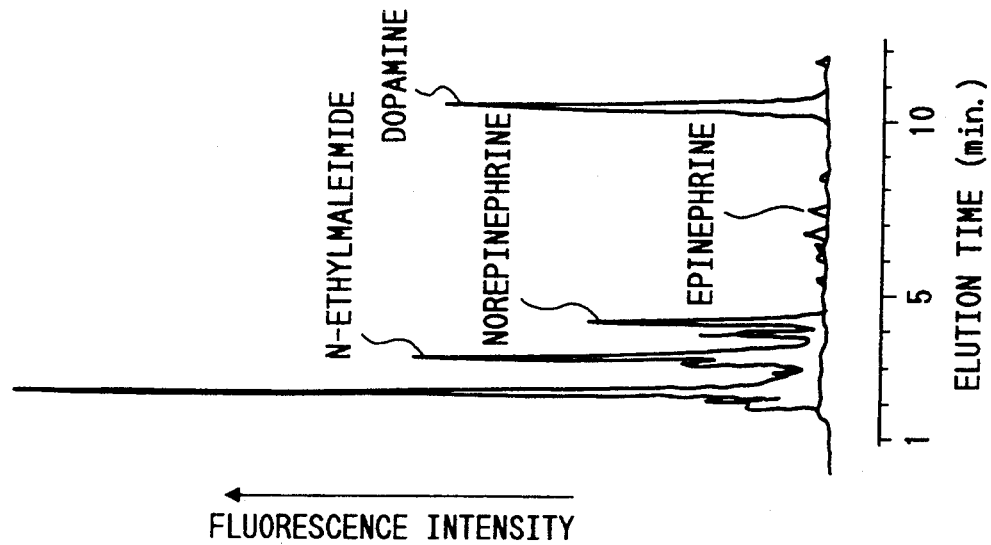
FIG. 4 illustrates a chromatogram of catecholamines contained in urine with the conventional N-ethylmaleimide added.

FIG. 4 illustrates the chromatogram when N-ethylmaleimide is added at the same concentration. Its peak was overlapped with that of the 3,4-dihydroxyphenylethyleneglycol (DOPEG) located a little before norepinephrine, showing a big peak. When maleimide was added, such a peak did not appear; DOPEG peak exhibited correct concentration, according to the finding of the present inventors.

This measuring method according to the present invention has been known to show a significant contribution to the elucidation of such phenomena as relationship existing between the concentration ratio of DOPEG to norepinephrine and neurocytoma. In this connection, since a great number of peaks are observed in this vicinity, peaks of the added reagent are preferred not to occur.

Figure 5:
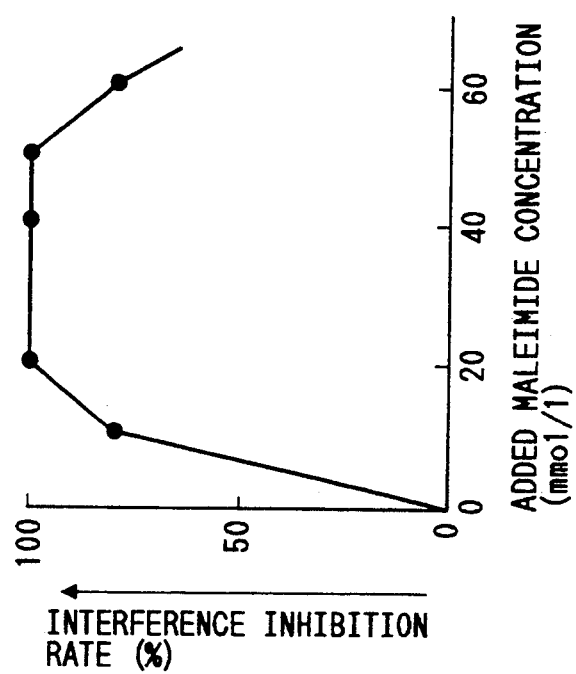
FIG. 5 is a graph representing the relationship between maleimide solution concentration and its interference inhibition rate, measured with a urine sample.

FIG. 5 illustrates the relationship between the maleimide solution concentration and interference inhibiting ratio, measured in terms of the urine sample. As illustrated, addition of excessive maleimide causes the fluorescence inducing reaction to be restricted, so maleimide solution concentration should preferably be 10 to 60 m mol/l in terms of the value at the time of mixing. Especially when high precision measurement is required, 20 to 50 m mol/l is to be preferred.

Embodiment 2

5 ml of blood from the healthy person was sampled by a blood collecting tube, and blood plasma was separated immediately by the centrifugal separator. 1.5 ml of it was transferred into another tube. The blood plasma was put into the centrifugal system ultrafiltering tube (fractional molecular weight), and protein was removed by centrifugal separation at about 10,000 rpm in the pretreatment process. 1.0 ml of the blood plasma from which the protein had been removed was taken into another test tube, and 100 µl of 200 mM maleimide solution (pH 7.3) was added to it. After that, 400 µl of acetonitrile dilute sulfuric acid solution of 1% 1,2- diphenylethylenediamine and 400 μl of the mixed aqueous solution of potassium ferricyanide and ammonium molybdate were added to it, and were heated to 50° C., obtaining fluorescence inductor in five minutes.

Similar to the case of embodiment 1, the high speed liquid chromatography device was used for separation and measurement. As a result, peaks which occurred when N-ethylmaleimide was added did not appear. The interference inhibition effect was almost 100% as in the case of urine. It is highly probable that the interfering component is different from that contained in the urine. Likewise, maleimide succeeded in inhibiting interference of fluorescence inducing reaction.

Embodiment 3

In the pretreatment process for blood plasma without protein in Embodiment 2, the maleimide sealed and preserved in separate glass-made small bottles and its solution were mixed immediately before use and were added. Maleimide sealed and preserved for over 6 months and its solution also gave the same results as that of Embodiment 2. Stable results can be ensured even by two substances having been kept separated for a long time, according to the finding of the present inventors.

Embodiment 4

A device comprising the high speed liquid chromatography device shown in FIG. 1, combined with auto sampler was prepared to conduct the measurement in Embodiment 1. The maleimide solution bottle and sample bottle were provided with auto sampler nozzles, and a specified volume of these solutions were sucked and discharged into the mixture reagent bottle, where they were mixed. 200 μl of acetonitrile dilute sulfuric acid solution of 1% 1,2-diphenylethylenediamine and 200 μl of the mixed aqueous solution of potassium ferricyanide and ammonium molybdate were added to 500 μl of this sample mixture, and were heated to 50° C., obtaining fluorescence inductor in five minutes. Then they were separated by the separator column, as in the case of Embodiment 1, gaining the identical the same results as those in Embodiment 1.

Use of the non-fluorescent maleimide to provide pretreatment in the measurement of catecholamines and their metabolites causes the maleimide to react with the coexisting measurement interfering substance, thereby preventing interference by that substance. This method ensures higher precision measurement than that of the conventional measuring method, without the maleimide itself producing any peak.

What is claimed is:

1. A liquid chromatographic fluorescence method of measuring a member of the group consisting of catecholamine and metabolites of catecholamine in a biological sample, said method comprising adding to said sample, before derivatizing said member of the group consisting of catecholamine and metabolites of catecholamine with a fluorescent agent, an amount of maleimide sufficient to increase accuracy of the peak identification.

2. A liquid chromatographic fluorescence method of measuring a member of the group consisting of catecholamine and metabolites of catecholamine in a biological sample, said method comprising, adding, before derivatizing said member of the group consisting of catecholamine and metabolites of catecholamine with a fluorescent agent, a specified volume of maleimide to said sample.

3. A liquid chromatographic fluorescence method of measuring a member of the group consisting of catecholamine and metabolites of catecholamine in a biological sample, said method comprising adding, before derivatizing said member of the group consisting of catecholamine and metabolites of catecholamine with a fluorescent agent, solid maleimide to a buffer solution and then adding said maleimide buffer solution to said sample.

4. A liquid chromatographic fluorescence method of measuring a member of the group consisting of catecholamine and metabolites of catecholamine in a biological sample, said method comprising, before derivatizing said member of the group consisting of catecholamine and metabolites of catecholamine with a fluorescent agent, adding maleimide to said sample while feeding at least one other derivatizing reagent into said sample.

5. A method of measuring at least one of a catecholamine and its metabolite according to claim 1, wherein concentration of said maleimide is 10 to 60 m mol/l in terms of concentration in a solution mixed with the biological sample.

6. A method of measuring at least one of a catecholamine and its metabolite according to claim 1, wherein concentration of said maleimide is 20 to 50 m mol/l in terms of concentration in a solution mixed with the biological sample.

7. A method of measuring at least one of a catecholamine and its metabolite according to claim 1, wherein the fluorescence inducing reagent contains at least one of ethylenediamine and 1,2-diphenylethylenediamine.

* * * * *